United States Patent [19]
Chwalisz et al.

[11] Patent Number: 5,906,987
[45] Date of Patent: May 25, 1999

[54] TREATMENT OF MALE CLIMACTERIC DISORDERS WITH NITRIC OXIDE SYNTHASE SUBSTRATES AND/OR DONORS, IN COMBINATION WITH ANDROGENS AND/OR AROMATASE INHIBITORS

[75] Inventors: Kristof Chwalisz, Berlin, Germany; Robert E. Garfield, Friendswood, Tex.

[73] Assignees: Schering Aktiengesellschaft and Board of Regents, Berlin, Germany; The University of Texas System, Austin, Tex.

[21] Appl. No.: 08/812,912

[22] Filed: Mar. 10, 1997

[51] Int. Cl.$^6$ .................. A61K 31/56; A61K 31/535; A61K 31/34; A61K 31/195; A61K 31/13
[52] U.S. Cl. .................. 514/177; 514/178; 514/236.2; 514/470; 514/565; 514/668
[58] Field of Search .................. 514/177, 178, 514/236.2, 470, 565, 668

[56] References Cited

U.S. PATENT DOCUMENTS

| | | | |
|---|---|---|---|
| 5,260,276 | 11/1993 | Cody et al. | 514/14 |
| 5,378,715 | 1/1995 | Stein et al. | 514/329 |

FOREIGN PATENT DOCUMENTS

| | | |
|---|---|---|
| 93/10144 | 5/1993 | WIPO . |
| 93/25580 | 12/1993 | WIPO . |
| 95/00537 | 1/1995 | WIPO . |
| 95/02408 | 1/1995 | WIPO . |
| 95/13802 | 5/1995 | WIPO . |
| WO95/13800 | 5/1995 | WIPO . |

OTHER PUBLICATIONS

Garfield et al., "Reversal of Preeclampsia Symptoms Induced in Rats by Nitric Oxide Inhibition With L–Arginine, Steroid Hormones and an Endothelin Antagonist," Soc. Gynecol. Invest. Abst. P384 (1994).

Chwalisz et al., "Estradiol Inhibits the Onapristone–Induced Preterm Parturition in Guinea Pigs by Blocking Cervical Ripening," J. Soc. Gynecol. Invest., vol. 2, No. 2, Mar. 1995., P101.

Chwalisz et al., "Role of Progesterone During Pregnancy: Models of Parturition and Preeclampsia," Z. Geburtshilfe Perinatol, vol. 198, No. 5–5, pp. 170–180, 1994.

Richard et al., "Vivo Evidence of an Endothelin–Induced Vasopressor Tone After Inhibition of Nitric Oxide Synthesis in Rats," Circulation, vol. 91, No. 3, pp. 771–775, Feb. 1995.

Yallamapalli et al., Inhibition of Nitric Oxide Synthesis in Rats During Pregnancy Produces Signs Similar to Those of Preeclampsia, Am J Obstet. Gynecol, vol. 169, No. 5, pp. 1316–1320, 1993.

Yallampalli et al., "Uterine Contractile Responses to Endothlin–1 and Endothelin Receptors are Elevated During Labor," Biol Reprod, vol. 51, No. 4, pp. 640–645, 1994.

*Primary Examiner*—Kimberly Jordan
*Attorney, Agent, or Firm*—Millen, White, Zelano & Branigan, P.C.

[57] ABSTRACT

The symptoms of climacterium in male mammals, e.g., hypertension, cardiovascular disease and osteoporosis, are ameliorated by the administration to an afflicted individual one or both of a nitric oxide substrate and/or nitric acid donor, in combination with an androgen, an aromatase inhibitor or both, wherein the circulating levels of testosterone in the afflicted individual are increased.

30 Claims, 2 Drawing Sheets

TREATMENT OF MALE CLIMACTERIC DISORDERS WITH NITRIC OXIDE SYNTHASE SUBSTRATES AND/OR DONORS, IN COMBINATION WITH ANDROGENS AND/OR AROMATASE INHIBITORS

BACKGROUND OF THE INVENTION

This invention relates to a method for the treatment and prevention of climacteric disorders during aging in males, such as increased incidence of cardiovascular diseases, etc., which may be associated with the continuous reduction in serum testosterone levels in men as they age, and becomes problematic in middle-age, with a nitric oxide synthase substrate (e.g., L-arginine), a nitric oxide donor or both, in combination with androgen hormone replacement therapy (HRT) and/or an aromatase inhibitor, which provides an increase in endogenous testosterone levels.

It is now well known that HRT, such as estrogen treatment, improves or reverses the adverse effects of the decrease in sex steroid secretion by the ovaries during menopause in women. Estrogens have also been shown to improve mood and psychological well-being in postmenopausal women and they also prevent atrophic changes in the genital tract. Estrogens have been shown to effect arterial tone and this may help to explain the reduction in hot flushes observed in postmenopausal women with estrogen therapy.

One of the most exciting recent advances in biology and medicine is the discovery that nitric oxide is produced by endothelial cells and that it is involved in the regulation of vascular tone, platelet aggregation, neurotransmission and immune activation (Furchgott and Zawadzki, 1980; Moncada, Palmer and Higgs, 1991; Ignarro, 1991). Nitric oxide is an important mediator of relaxation of the muscular smooth muscle (Montada, Palmer and Higgs, 1991) and was formerly known as EDRF (endothelin-derived relaxing factor) (Furchgott and Zawadzki, 1980; Moncada, Palmer and Higgs, 1991). Nitric oxide is synthesized by the oxidative deamination of a guanidino nitrogen of L-arginine by at least three different isoforms of a flavin-containing enzyme, nitric oxide synthase (Moncada, Palmer and Higgs, 1991). Synthesis of nitric oxide has been shown to be competitively inhibited by analogues of L-arginine; NG-nitro-L-arginine methyl ester (L-NAME), NG-monoethyl-L-arginine (LMMA), N-iminoethyl-L-ornithine (L-NIO), L-monomethyl-L-arginine (L-NNMA) and L-NG-methylarginine (LNMA) and Nw-nitro-L-arginine (L-NA).

Nitric oxide elevates levels of cGMP (1,3,5-cyclic guanosine monophosphate) within the vascular smooth muscle to produce relaxation and to reduce blood vessels tone (Moncada, Palmer and Higgs, 1991). Nitric oxide binds to heme and thus activates soluble guanylate cyclase (Ignarro, 1991) to increase the cellular content of cGMP. It has long been recognized that nitrovasodilators, such as nitroprusside and nitroglycerin, inhibit vascular smooth muscle contractility to produce relaxation or to reduce vascular tone. These agents have been used since the late 1800's as vasodilators. However, only recently has the mechanism of action of these compounds been realized. Nitrovasodilators are now classified as nitric oxide donors because they are metabolized to release nitric oxide (Moncada, Palmer and Higgs, 1991). The long-used nitrovasodilators may be regarded as substitution therapy for a failing physiological mechanism. Nitric oxide is also produced by macrophages and other immune cells.

There is a substantial body of evidence from animal experiments that a deficiency in nitric oxide contributes to the pathogenesis of a number of diseases, including hypertension, atherosclerosis and diabetes, and erectile dysfunction in men (Moncada, Palmer and Higgs, 1991). There are many recent studies showing that the inhibition of nitric oxide synthase dramatically increases blood pressure. The inhibition of nitric oxide synthesis with L-NNMA, L-NA or L-NAME causes long-lasting elevation in blood pressure and suggests that its reduction may contribute to the pathogenesis of hypertension (Moncada and Palmer, 1992). Furthermore, L-NAME-treatment potentiates presser responses to angiotensin II, vasopressin and norepinephrine. Also, in patients with pregnancy-induced hypertension, release of nitric oxide by umbilical vessels in blunted (Pinto et al, 1991) and the physiological decrease in blood pressure in pregnant spontaneous hypertensive rats was shown to depend on endothelial nitric oxide (Ahokas, Merces and Sibai, 1991). Additionally, infusion of L-NA increases blood-pressure in pregnant rats and potentiates responses to vasopressors (Molnar and Hertelendy, 1992). These studies suggest that impaired nitric oxide synthesis may be an important mechanism in the etiology of cardiovascular problems.

Nitric oxide synthesis and nitric oxide effector system (cGMP-dependent relaxation mechanism) are thought to be regulated by steroid hormones. There is an increase in cardiovascular diseases in women following menopause and which may be related to the decrease in sex steroids and an alteration in nitric oxide. Female steroid hormones have been shown to modulate endothelium-dependent relaxation of vascular smooth muscle by nitric oxide. Estradiol treatment of rats causes increased nitric oxide production by vascular tissues, whereas progesterone counteracts this phenomenon (Miller and Van Houtte, 1991). It is well known that pregnancy is associated with an increase in cardiac output and a decrease in the resistance of virtually all the vascular beds in the body. Although the mechanism of this phenomenon is not known, it could be associated with changes in nitric oxide production or effects as a result of elevated steroid hormone levels. One important observation with regard to the above mechanism is that antiprogestins (RU 486) elevate blood pressure in animals (Kalimi, 1989) and they produce hot flushes in humans, both males (Grunberg et al., 1993) and females (Kettel et al., 1991). The hot flushes may be mediated by the steroid action on the release of nitric oxide. Hot flushes are a primary symptom in menopausal and postmenopausal women and they are relieved by both estrogen and progesterone (Avis et al., 1993).

Another symptom of climacterium in both men and women is osteoporosis. There is also growing evidence that nitric oxide mediates steroid (estrogen and/or progestin) effects on bones (C. W. G. M. Löwik et al., J. Clin. Invest., 93:1465–1472 (1994); T. P. Kasten et al., Proc. Natl. Acad. Sci. USA 88:2936–2940 (1991); M. Zaidi et al., Bone 14:97–102 (1993); A. S. M. Towhidul Alam et al., Bioscience Reports 12:369 (1992)).

The studies described in U.S. patent application Ser. No. 153,345, filed Nov. 16, 1993, show that nitric oxide and the subsequent relaxation of the uterus is controlled by progesterone. The relaxation effects of the nitric oxide substrate, L-arginine, are greater in late pregnancy when progesterone levels are elevated in pregnant rats. Also there is greater uterine relaxation with L-arginine when uterine strips are taken from nonpregnant, ovariectomized rats treated with progesterone. In addition, treatment with pregnant rats with the nitric oxide inhibitor produces signs and symptoms of preeclampsia (e.g., hypertension, fetal retardation and proteinuria—the classical triad of preeclampsia). These symptoms are related to the decrease in vascular resistance and placental perfusion. Preeclampsia is a well known model of atherosclerosis as the decrease in placental perfusion is accompanied by increased fibrin deposition in placental vessels and increased thrombus formation (Roberts et al., 1989). Thus, nitric oxide substrates and/or donors alone or in combination with estrogen and progesterone are particularly efficacious for hormone replacement therapy to prevent climacteric symptoms (climacterium) such as atherosclerosis, hypertension, hot flushes, etc. in women.

EP 0441 119 A2 discloses the use of L-arginine in the treatment of hypertension and other vascular disorders. It suggests that the mechanism by which L-arginine is effective for this purpose is because it may be the physiological precursor of "the most powerful endothelial-derived releasing factor, nitric oxide." The use of L-arginine in combination with other pharmaceutically active agents is not discussed in this publication.

SUMMARY OF THE INVENTION

In a method aspect, this invention relates to a method of treating climacterium (climacteric symptoms) in a male mammal, comprising administering to a patient in need of such treatment an effective amount of (a) at least one of a nitric oxide synthase substrate, a nitric oxide donor, or a compound which stimulates nitric oxide synthesis in target cells, and (b) an androgen or an aromatase inhibitor, or both.

In a product aspect, this invention relates to pharmaceutical compositions comprising an admixture of effective amounts of (a) at least one of a nitric oxide synthase substrate, a nitric oxide donor, or a compound which stimulates nitric oxide synthesis in target cells, (b) an androgen or an aromatase inhibitor, or both.

It is thus an object of the invention to provide a method for the prevention and treatment of climacterium (climacteric symptoms), including cardiovascular disease, hypertension, impotence and osteoporosis, in male mammals, e.g., humans, with a nitric oxide substrate and/or donor, in combination with an androgen and/or an aromatase inhibitor, which method provides an increase in endogenous testosterone levels.

It is a further object to provide a method for hormone replacement therapy (HRT) in male mammals, e.g., humans, with a nitric oxide substrate and/or donor, in combination with an androgen and/or an aromatase inhibitor, which method provides an increase in testosterone levels.

A further object is the provision of pharmaceutical compositions useful in practicing the methods of this invention.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, wherein.

DETAILED DISCLOSURE

Figure 1:
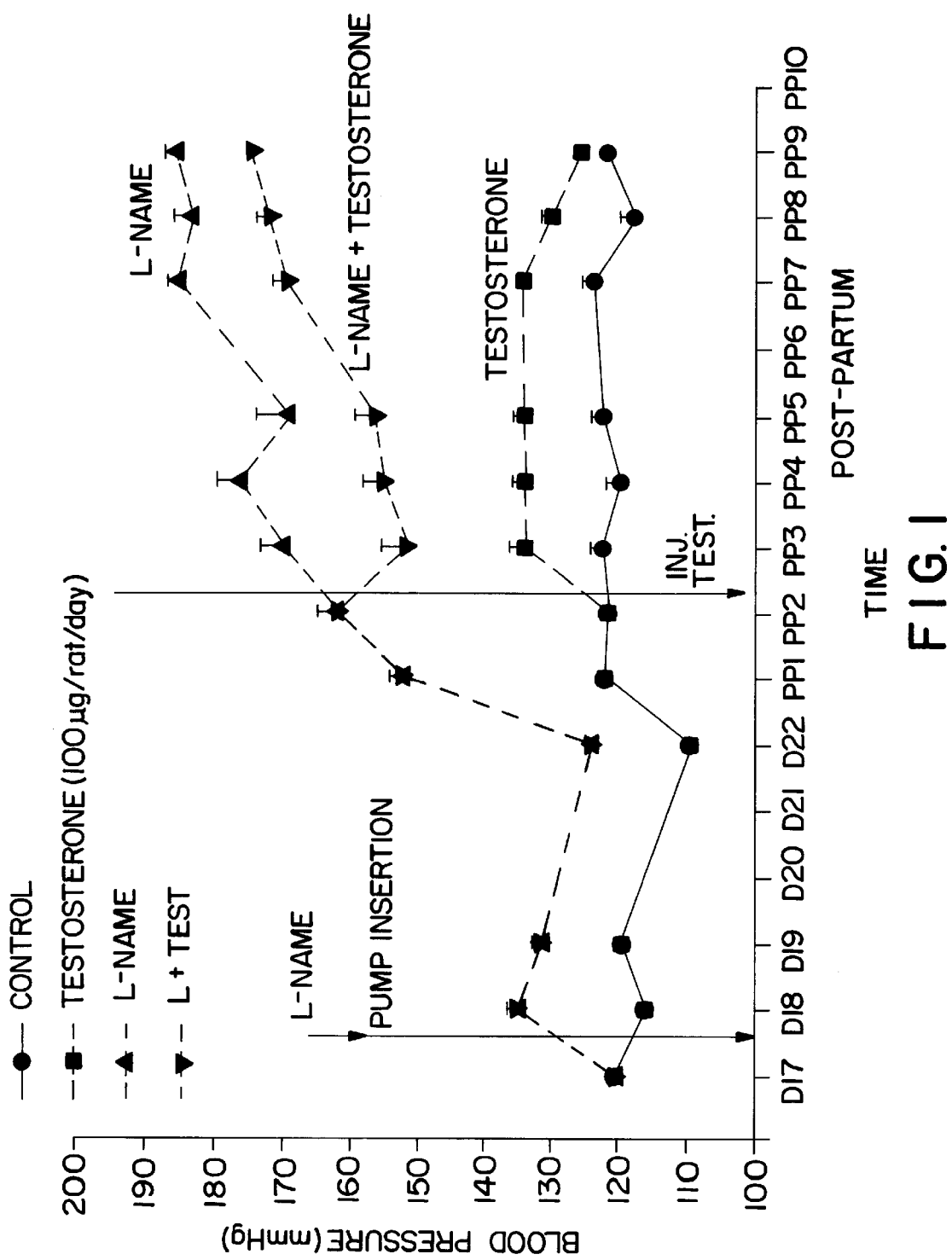
FIG. 1 shows the effect of testosterone on blood pressure in L-NAME-treated rats post-partum. The control group (●) received only the vehicles. The testosterone-only group (■) was treated with 100 μg/rat/day, s.c., starting on day 2 postpartum. The L-NAME only group (▲) was treated with 50 mg/rat/day, s.c., continuous infusion, starting on day 17 of pregnancy. The L-NAME+testosterone group (▼) was treated with 50 mg/rat/day of L-NAME, s.c., continuous infusion, starting on day 17 of pregnancy, and with 100 μg/rat/day of testosterone, s.c., starting on day 2 post-partum.

The methods and pharmaceutical compositions of this invention treat climacterium (climacteric symptoms) in an aging male mammal, e.g., in a male human, who is manifesting the symptoms thereof or who is a high risk candidate for doing so, e.g., based on increased blood pressure. The invention employs either or both of a nitric oxide synthase substrate (e.g, L-arginine) and a nitric oxide donor (e.g., sodium nitroprusside or glyceryl trinitrate), and/or a compound which stimulate nitric oxide synthesis in the target cells, in combination with one or more of an androgen (e.g., testosterone or testosterone ester) and an aromatase inhibitor (e.g., atamestane).

During our research on these various conditions, it was unexpectedly found that androgens, e.g., testosterone and 5α-dihydrotestosterone (DHT), partially compensate for the L-NAME-induced increase in blood pressure in post-partum female rats. This is particularly surprising in view of the fact that both androgens slightly increased blood pressure in rats which did not receive L-NAME. These results indicate that androgens, similarly to progestins, induce compensatory mechanisms when nitric oxide synthesis is blocked or reduced. These results strongly suggest that androgens, as well as compounds such as aromatase inhibitors, which increase the endogenous androgen levels in male mammals, modulate nitric oxide synthesis or activity, as do estrogens and progestins. These results further implicate the physiological role of testosterone in the development of pathological conditions occurring during aging in male mammals, e.g., humans, including cardiovascular disease, dementia, etc.

Because these abnormal conditions of aging in male mammals, e.g., humans, are produced by or aggravated by subnormal nitric oxide synthesis, both nitric oxide synthase substrates, e.g., L-arginine, and nitric oxide donors, e.g., sodium nitroprusside, nitroglycerin, glycerin trinitrate, SIN-1, isosorbid mononitrate, isosorbid dinitrate and diethylenetriamine/NO (DETA/NO), are useful for ameliorating the symptoms thereof and, in one aspect of the method of this invention, a combination of both are employed. In addition, or instead, compounds which stimulate nitric oxide synthesis in the target cells, e.g., epithelial and/or brain nitric oxide synthase (eNOS and bNOS) stimulators, can be employed.

An additional effect is achieved when an androgenic agent is administered concurrently with the nitric oxide substrate and/or nitric acid donor. Thus, an androgen (e.g., testosterone or testosterone ester) and/or an aromatase inhibitor (e.g., atamestane) are administered concurrently with the nitric oxide-increasing agents, e.g., in amounts effective to raise blood serum total testosterone level to between about 100 and about 600 mg/dl.

Thus, in a method aspect, this invention relates to a method of treating the climacterium symptoms in a male mammal, which comprises administering to an individual manifesting the symptoms thereof at least one of a nitric oxide donor, a nitric oxide synthase substrate, or a compound which increases synthesis of NO in target cells, in combination with one or both of an androgen and an aromatase inhibitor, in amounts effective to ameliorate the symptoms thereof. For treatment of a human male, the amount of the nitric oxide synthase substrate, nitric oxide donor or both administered is effective to, respectively, either raise the blood level of circulating L-arginine in a male to whom the composition is administered to at least about 10–50 nmole above the normally 50–100 nmolar circulating levels or raise nitric oxide donor levels to about 1–1000 nmolar. The androgen and/or aromatase inhibitors are administered concurrently with the nitric oxide-increasing agents, e.g., for testosterone, in amounts effective to raise blood serum total testosterone level to between about 100 and about 600 mg/dl, and/or, for aromatase inhibitors, in an amount effective to raise endogenous testosterone levels by at least 30%.

In a product aspect, this invention relates to a pharmaceutical composition comprising effective amounts of at least one of a nitric oxide synthase substrate, a nitric oxide donor, or a compound which increases synthesis of NO in target cells, in combination with at least one of an androgen and an aromatase inhibitor. For treatment of a human male, the amount of the nitric oxide synthase substrate, a nitric oxide donor or both per unit dosage is effective to, respectively, either raise the blood level of circulating L-arginine to at least about 10–50 nmole above the normally 50–100 nmolar circulating levels or raise the nitric oxide donor levels to about 1–1000 nmolar. The androgen and/or aromatase inhibitors are administered concurrently with the nitric oxide-increasing agents, e.g., for testosterone, in amounts effective to raise blood serum total testosterone level to between about 100 and about 600 mg/dl, and/or, for aromatase inhibitors, in an amount effective to raise endogenous testosterone levels by at least 30%.

Examples of dosage ranges of typical NO-substrates and NO-donors (per os or transdermally) are:

|  | total dose: |
| --- | --- |
| L-Arginine | 500 mg - 10 g p.o. |
| Sodium Nitroprusside | range 500–2000 μg/kg/day p.o. |
| Nitroglycerin | 0.5–10 mg p.o. |
| Nitroglycerin | 0.1–10 mg/24 hours transdermal |
| Isosorbid mononitrate | 10–100 mg/day p.o. |
| Isosorbid dinitrate | 10–100 mg/mg p.o. |

The nitric oxide donors (e.g., nitroglycerin) can be administered preferentially by a transdermal patch (e.g., Deponit 5/10/T [Schwarz Pharma], Nitroderm TTS 5/Nitroderm TTS 10 [CIBA]), orally (e.g., Corangin [CIBA], Nitrolingual forte or mitte [Pohl]), etc.

Examples of dosages for typical androgens (per os or transdermally) are:

|  | total dose: |
| --- | --- |
| Testosterone | 1–10, preferably 4–6 mg/day transdermal |
| Testosterone esters: | |
| Testosterone propionate | 10–250 mg i.m. every 2–4 weeks |
| Testosterone propionate | 10–100 mg i.m. 2–3x/week |
| Testosterone enanthate | 10–250 mg i.m. every 2 weeks |
| Testosterone cypionate | 10–250 mg i.m. every 1–3 weeks |
| Testosterone undecanoate | 20–200 mg/day p.o. |
| Mesterolon | 25–200 mg/day p.o. |
| Methyltestosterone | 1–100 mg/day p.o. |

Examples of suitable androgens are: Testosterone: Testoderm, Alza Pharmaceuticals, testosterone transdermal system, release rate 4 and 6 mg/day, preferably 4 mg/day; testosterone propionate: Testoviron-Depot-250, Schering; testosterone enanthate: Delatestryl; testosterone cypionate: Depo-Testosterone, Upjohn; testosterone undecanoate: Andriol, Organon; Mesterolon: Proviron 25, Schering.

As typical aromatase inhibitors, all compounds are suitable that are suitable as substrates for aromatase, such as, for example: the testolactone (17a-oxa-D-homo-androst-1,4-diene-3,17-dione) that is described in the "Journal of Clinical Endocrinology and Metabolism," 49, 672 (1979), the compounds androsta-4,6-diene-3,17-dione, androsta-4,6-dien-17β-ol-3-one acetate, androsta-1,4,6-triene-3,17-dione, 4-androstene-19-chloro-3,17-dione, 4-androstene-3,6,17-trione that are described in "Endocrinology" 1973, Vol. 92, No. 3, page 874; the 19-alkynylated steroids that are described in German Laid-Open Specification 31 24 780, the 10-(1,2,-propadienyl)-steroids that are described in German Laid-Open Specification 31 24 719; the 19-thio-androstane derivatives that are described in European patent application, publication no. 100 566; the 4-androsten-4-ol-3,17-dione and its esters that are described in "Endocrinology" 1977, Vol. 100, No. 6, page 1684 and U.S. Pat. No. 4,235,893; the 1-methyl-15α-alkyl-androsta-1,4-diene-3,17-dione that is described in German Laid-Open Specification 35 39 244; the 10β-alkinyl-4,9(11)-estradiene derivatives that are described in German Laid-Open Specification 36 44 358; and the 1,2β-methylene-6-methylene-4-androstene-3,17-dione that is described in European Patent Application 0 250 262.

According to this invention, selective aromatase inhibitors are preferably used for the production of a pharmaceutical agent for treating a relative androgen deficiency in men. Selective aromatase inhibitors are deemed as those compounds that act as substrates for the aromatase and at the dosage used affect no enzyme other than aromatase in a clinically relevant way.

Regarded as typical selective aromatase inhibitors according to this invention are, for example, the steroidal compounds 1-Methyl-androsta-1,4-diene-3,17-dione (DE-A 33 22 285; atamestane); 4-hydroxy-4-androstene-3,17-dione (formestane); as well as the non-steroidal aromatase inhibitors: (RS)-5-(4-cyanophenyl)-5,6,7,8-tetrahydro-imidazo-(1,5α)-pyridine, hydrochloride (Cancer Res., 48, pp. 834–838, 1988: fadrozole); 4-[cyano-α-(1,2,4-triazol-1-yl)-benzyl]-benzonitrile (CGS 20267), 5-[cyclopentylidene-(1-imidazolyl)-methyl]-thiophene-2-carbonitrile(EP-A 0 411 735; pentrozole); 2,2'-[5-(1H',2',4-triazol-1-yl-methyl)-1,3-phenylene]-bis(2'-methylpropionitrile) (arimidex); and (6-[1-(4-chlorophenyl)-1,2,4-triazol-1-yl)-methyl]-1-methyl-1H-benzotriazole, dihydrochloride (vorozole).

The list of selective aromatase inhibitors above is not exhaustive; other compounds that are described in the above-mentioned materials and publications, as well as all other compounds that meet the set requirements, are also included.

Examples of dosage ranges of typical aromatase inhibitors (per os or transdermally) are:

|  | total dose: |
| --- | --- |
| Atamestane | 20–200 mg/day |

In general, suitable dosages of aromatase inhibitors are those which, when administered to a male in conjunction with an NO donor and/or substrate, raise the endogenous testosterone levels by at least 30%. Typical dosages of aromatase inhibitors are those bioequivalent to 20–200 mg/day of atamestane, optionally together with an androgen at a daily dosage bioequivalent to about 1–10 mg of testosterone per day transdermally.

Many other examples of compounds in each of the foregoing categories are well known and can be employed in this invention.

The pharmacologically active agents employed in this invention can be administered in admixture with conventional excipients, i.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parental application, particularly suitable are solutions, preferably oily or aqueous solutions, as well as suspensions, emulsions, or implants, including suppositories, transdermal patches, and vaginal gels, creams and foams. Ampoules are convenient unit dosages. In a preferred aspect, the composition of this invention is adapted for ingestion.

For enteral application, particularly suitable are unit dosage forms, e.g., tablets, dragees or capsules having talc and/or carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet or dragee contains, for example, 5–5000 mg of each active agent. Solutions for parenteral administration contain, e.g., 0.01–1% of each active agent in an aqueous or alcoholic solution.

The nitric oxide substrate and/or donor can be administered as an admixture with an androgen and/or aromatase inhibitor and/or any other optional active agent or as a separate unit dosage form, either simultaneously therewith or at different times during the day from each other.

The combination of active agents is preferably administered at least once daily (unless administered in a dosage form which delivers the active agents continuously) and more preferably several times daily, e.g., in 2 to 6 divided doses. The typical dose is about 0.5 to 1000 mg of each active agent, although some less active agents, e.g., L-arginine, require much higher oral dosages, e.g., 500 to 10,000 mg, and others, e.g., sodium nitroprusside, require lower doses, e.g., 500–2,000 µg/kg/day. Doses for nitroglycerine typically are orally 2.6 mg 2×daily; sublingually, 0.8 mg, 1–4×daily; and transdermally, 0.2–0.5 mg/hr. Since the $LD_{50}$ dosages of most of these active agents is known in the prior art, a lower dosage regimen can be initiated and the dosage increased until a positive effect is achieved or a higher dosage regimen can initially be employed, e.g., in a crisis situation, and the dosages regulated downward as relief from the symptoms is achieved. Combinations of agents can be employed either continuously or sequentially.

In humans, both L-arginine and testosterone (or a bioequivalent of another androgen) and/or atamestane (or a bioequivalent amount of another aromatase inhibitor) should be given in a ratio which produces blood plasma levels of about 50–5000 µmolar L-arginine, and about 100–600 mg/dl testosterone. For the aromatase inhibitors, the dosage should be effective to raise the endogenous testosterone levels by at least 30%.

In the experiments whose results are shown by the graph of FIG. 1, female pregnant rats were divided into four groups (n=6/group) and treated as detailed in the description of FIG. 1, above. In the control group, a typical pattern of blood pressure (low values during pregnancy and an increase postpartum) was observed. Treatment with testosterone alone led to the increase in blood pressure post-partum. Treatment with L-NAME alone showed a typical pattern of blood pressure: a slight increase during pregnancy and a sharp increase postpartum. Post-partum administration of testosterone to the L-NAME-treated animals attenuated the L-NAME-induced increase in blood pressure.

Figure 2:
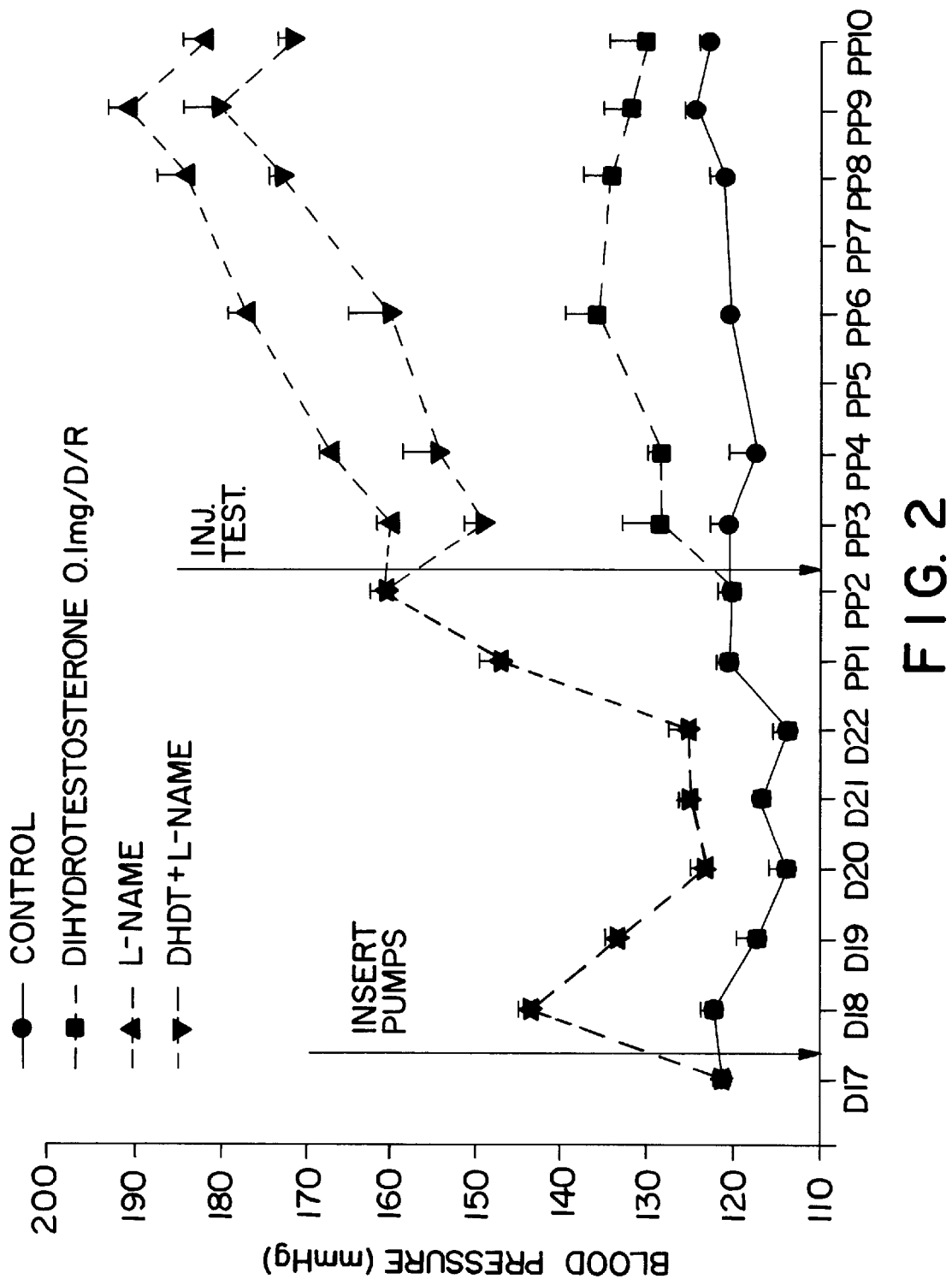
FIG. 2 shows the effect of 5α-dihydrotestosterone on blood pressure in L-NAME-treated rats post-partum. The control group (●) received only the vehicles. The dihydrotestosterone-only group (■) was treated with 100 μg/rat/day, s.c., starting on day 2 postpartum. The L-NAME only group (▲) was treated with 50 mg/rat/day, s.c., continuous infusion, starting on day 17 of pregnancy. The L-NAME+dihydrotestosterone group (▼) was treated with 50 mg/rat/day of L-NAME, s.c., continuous infusion, starting on day 17 of pregnancy, and with 100 μg/rat/day of dihydrotestosterone, s.c., starting on day 2 post-partum.

In the experiments whose results are shown by the graph of FIG. 2, female pregnant rats were divided into four groups (n=6/group) and treated as detailed in the description of FIG. 2, above. In the control group, a typical pattern of blood pressure (low values during pregnancy and an increase postpartum) was observed. Treatment with dihydrotestosterone alone led to the increase in blood pressure post-partum. Treatment with L-NAME alone showed a typical pattern of blood pressure: a slight increase during pregnancy and a sharp increase post-partum. Post-partum administration of dihydrotestosterone to the L-NAME-treated animals attenuated the L-NAME-induced increase in blood pressure.

It can be concluded from these studies that the effects of nitric oxide in male mammals are modulated by androgens. L-NAME is an inhibitor of nitric oxide synthesis, which is known to increase blood pressure in male mammals. It is known that blood pressure is improved in L-NAME treated rats given a nitric oxide substrate (L-arginine). L-arginine is the substrate for nitric oxide synthesis, which is known to reduce blood pressure; therefore, one can deduce that nitric oxide substrates as well as nitric oxide donors will also decrease blood pressure. Since nitric oxide is known to control atherosclerosis, that L-NAME-treatment is identical with preeclampsia, which is associated with other sclerosis, and that atherosclerotic hypertension is accelerated in climacterium, treatment with nitric oxide substrates and/or nitric oxide donors in combination with androgens and/or aromatase inhibitors will have tremendous advantages for climacterium therapy.

The results of these experiments on post-partum rats indicate that androgens, similarly to progestins, induce compensatory mechanisms when nitric oxide synthesis is blocked or reduced. Thus, since the blood pressure-increasing effects of L-NAME are partially compensated by androgens, it can be concluded that administration of a nitric oxide donor or a nitric oxide substrate may have greater effects when an nitric oxide substrate or donor are combined with an androgen or an aromatase inhibitor. These effects are not mediated by estrogens, since DHT cannot be converted to estradiol. These results strongly suggest that androgens, as well as compounds such as aromatase inhibitors, which increase the endogenous androgen levels in male mammals, modulate nitric oxide synthesis or activity, as do estrogens and progestins.

Without wishing to be bound by mechanism, a direct effect on the blood vessels is proposed. These results further implicate the physiological role of testosterone in the development of pathological conditions occurring during aging in male mammals, e.g., humans, including, e.g., cardiovascular disease, hypertension, osteoporosis, impotence, dementia, etc., as well as under circumstances wherein the normal testosterone-producing tissue is not functional, e.g., after orchidectomy.

The method of treatment employed in this invention can be employed for the treatment of hypertension, as an adjuvant in thrombotic disorders, and hemorrhage, etc., following the dosage regime described herein.

Without further elaboration, it is believed that one skilled in the art can, using the preceding description, utilize the present invention in its fullest extent. The preferred specific embodiments are, therefore, to be construed as merely illustrative, and not limitative of the disclosure in any way whatsoever.

The entire disclosure of all applications, patents and publications, cited above and below are hereby incorporated by reference.

EXAMPLES

Example 1

Treatment of Climacterium (Climacteric Symptoms)

To a human male (ca 50 years; 80–120 kg) displaying the signs of male climacterium symptoms, e.g., high blood pressure, osteoporosis, etc., administer 0.5–40 g of L-arginine per os daily, with an androgen, e.g., testosterone, 1 to 10 mg/day transdermally until the symptoms are ameliorated. Thereafter, administer 0.5 to 10 g of L-arginine and 1–10 mg/day, preferably 4 mg/day, of testosterone daily.

Example 2

Treatment of Climacterium (Climacteric Symptoms)

To a male comparable to and displaying the same symptoms as Example 1, administer daily 2×5 mg of nitroglycerine per os in place of L-arginine.

Example 3

Treatment of Climacterium (Climacteric Symptoms)

To a male similar to and displaying the same symptoms as Example 1, administer daily 5–10 mg of nitroglycerine transdermally with an androgen, testosterone, 1–10 mg per day transdermally.

Example 4

Hormone Replacement Therapy

To a male similar to and displaying the same symptoms as Example 1, administer daily 0.5–20 g of L-arginine in combination with an aromatase inhibitor in amounts sufficient to raise the endogenous testosterone levels by at least 30%, e.g., atamestane at 10–200 mg daily.

Example 5

Hormone Replacement Therapy

To a male after orchidectomy, administer L-arginine 0.5 to 20 g daily and/or a nitric oxide donor, e.g., nitroglycerine at 2×2.5 mg daily with one or more of the following: an androgen, e.g., transdermal testosterone at 4 mg/day or testosterone propionate at 250 mg i.m. 2–3 times/week, and/or an aromatase inhibitor, e.g., atamestane at 20–200 mg/day. The sex steroids and/or aromatase inhibitor are to be given either continuously with L-arginine and/or a nitric oxide donor, or sequentially.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

REFERENCES

1. Barbieri, R. L. The bladder in menopause: Lower urinary tract dysfunction during the climacteric. Curr. Problems Obstet. Gynecol. Fertil. 1994; 17(6):196–228.
2. Eli, G. and Bergman, A. Estrogen effects on the urethra: beneficial effects in women with genuine stress incontinence. Obstet. Gynecol. 1993; 48(7):509–517.
3. Sartori, M. G., Baracat, E. C., Girad, M. J., Gonccalves, W. J., Sartori, J. P., de Lima, G. R. Menopausal genuine stress urinary incontinence treated with conjugated estrogens plus progestogens. Int. J. Gynecol. Obstet. 1995; 49(2):165–169.
4. Cardozo, L. D. and Kelleher, C. J. Sex hormones, the menopause and urinary problems. Gynecol. Endocrinol. 1995; 9(1):75–84.
5. Cardozo, L. and Kelleher, C. Sex hormones and the female lower urinary tract. Physiotherapy 1994; 80:135–138.
6. Brandeis, G. H. and Resnick, N. M. Pharmacotherapy of urinary incontinence in the elderly. Drug Therapy 1992; 22:93–102.
7. Furchgott, R. F. and Zawadzki, J. V. The obligatory role of endothelial cells in the relaxation of arterial smooth muscle by acetylcholine. Nature 1980; 288:373–376.
8. Moncada, S., Palmer, R. M. G. and Higgs, E. A. Nitric oxide; physiology, pathophysiology and pharmacology. Pharmacol. Rev. 1991; 43:109–142.
9. Ignarro, L. J. Physiological significance of Nitric oxide. Seminars in Perinatology 1991; 15:20–26.
10. Ehren, I., Adolfsson, J. and Wilund, N. P. Nitric oxide synthase activity in the human urogenital tract. Urol. Res. 1994; 22:287–290.

11. Andersson, K. E. and Persson, K. Nitric oxide synthase and nitric oxide mediated effects in lower urinary tract smooth muscles. World J. Urol. 1994; 12:274–280.
12. Smet, P. J., Edyvane, K. A., Jonavicius, J., Marshall, V. R. Distribution of NADPH-diaphorase-positive nerves supplying the human urinary bladder. J. Autonomic Nervous System 1994; 47:109–113.
13. Lee, J. G., Wein, A. J., Levin, R. M. Comparative pharmacology of the male and female rabbit bladder neck and urethra: Involvement of nitric oxide. Pharmacology
14. Chwalisz, K. and Garfield, R. E. Role of progesterone during pregnancy: Models of parturition and preeclampsia. Z. Geburtsh. u. Perinat. 198:170–180.

What is claimed is:

1. A method of treating climacteric symptoms in a male mammal, comprising administering to a patient in need of such treatment an effective amount of
    (a) at least one of a nitric oxide synthase substrate, a nitric oxide donor, or a compound which stimulates nitric oxide synthesis in target cells,
    (b) an androgen or an aromatase inhibitor, or both.
2. A method of claim 1, wherein the mammal is a human male suffering from symptoms of androgen deprivation.
3. A method of claim 1, wherein the mammal is a human male who has exhibited a need for or is a candidate for hormone replacement therapy.
4. A method of claim 1, wherein the mammal is a human male and a nitric oxide synthase substrate is administered thereto.
5. A method of claim 4, wherein the nitric oxide substrate is L-arginine.
6. A method of claim 1, wherein the mammal is a human male and a nitric oxide donor is administered thereto.
7. A method of claim 6, wherein the nitric oxide donor is sodium nitroprusside, nitroglycerin, glyceryltrinitrate, SIN-1, isosorbid mononitrate or isosorbid dinitrate.
8. A method of claim 6, wherein the nitric oxide donor is administered orally.
9. A method of claim 6, wherein the nitric oxide donor is administered transdermally as a patch.
10. A method of claim 1, wherein the androgen is testosterone or a testosterone ester.
11. A method of claim 10, wherein the androgen is administered orally.
12. A method of claim 10, wherein the androgen is administered transdermally as a patch.
13. A method of claim 10, wherein the androgen is administered intramuscularly or subcutaneously.
14. A method of claim 1, wherein the mammal is a human male and an aromatase inhibitor is administered thereto.
15. A method of claim 1, wherein the mammal is a human male and the amount of the nitric oxide synthase substrate, nitric oxide donor or both administered is effective to raise the blood level of circulating L-arginine in a male to whom the composition is administered to at least about 10–50 nmole above the normally 50–100 nmole circulating levels and/or to raise the nitric oxide donor level to about 1–1000 nmolar.
16. A method of claim 1, wherein the mammal is a human male and the amount of an androgen, an aromatase inhibitor or both administered is effective to raise blood serum total testosterone level to between about 100 and about 600 mg/dl.
17. A method of claim 1, wherein components (a) and (b) are administered sequentially.
18. A method of claim 1, wherein components (a) and (b) are administered simultaneously.
19. A method of claim 1, wherein the male mammal is a human suffering from or at risk of developing symptoms of osteoporosis.
20. A method of claim 1, wherein the male mammal is a human suffering from or at risk of developing hypertension.
21. A method of claim 1, wherein the male mammal is a human suffering from or at risk of developing cardiovascular disease.
22. A pharmaceutical composition comprising an admixture of effective amounts of
    (a) at least one of a nitric oxide synthase substrate, a nitric oxide donor, or a compound which stimulates nitric oxide synthesis in target cells,
    (b) an androgen or an aromatase inhibitor or both.
23. A composition of claim 22, wherein (a) comprises a nitric oxide synthesis substrate.
24. A composition of claim 23, wherein the nitric oxide synthesis substrate is L-arginine.
25. A composition of claim 22, wherein (a) is a nitric oxide donor.
26. A composition of claim 25, wherein the nitric oxide donor is sodium nitroprusside, nitroglycerin, glyceryltrinitride, SIN-1, isosorbid mononitrate or isosorbid dinitrate.
27. A composition of claim 22, wherein (b) is an androgen.
28. A composition of claim 22, wherein the androgen is testosterone or testosterone propionate.
29. A composition of claim 22, wherein (b) is an aromatase inhibitor.
30. A composition of claim 29, wherein the aromatase inhibitor is atamestane.

* * * * *